United States Patent [19]

Thoene

[11] Patent Number: 5,056,221
[45] Date of Patent: Oct. 15, 1991

[54] RAZOR AND PROCESS FOR MANUFACTURING A SURFACE OF LOW FRICTIONAL RESISTANCE ON A RAZOR

[75] Inventor: Jochen Thoene, Wuppertal, Fed. Rep. of Germany

[73] Assignee: Wilkinson Sword GmbH, Solingen, Fed. Rep. of Germany

[21] Appl. No.: 626,402

[22] Filed: Dec. 14, 1990

Related U.S. Application Data

[63] Continuation of Ser. No. 285,175, Dec. 16, 1988, abandoned.

[30] Foreign Application Priority Data

Dec. 19, 1987 [DE] Fed. Rep. of Germany ....... 3743298

[51] Int. Cl.$^5$ .............................................. B26B 19/44
[52] U.S. Cl. .......................................... 30/41; 30/50; 424/73; 525/127
[58] Field of Search .................. 30/32, 41, 50, 83, 84, 30/85; 427/388.1, 388.4, 388.5; 424/73; 525/127

[56] References Cited

U.S. PATENT DOCUMENTS

| | | | |
|---|---|---|---|
| 3,715,942 | 2/1973 | Courtney . | |
| 3,903,410 | 9/1975 | Akrongold et al. . | |
| 4,100,309 | 7/1978 | Micklus et al. | 525/127 |
| 4,170,821 | 10/1979 | Booth | 30/41 |
| 4,381,293 | 4/1983 | Michel | 424/14 |
| 4,416,924 | 11/1983 | Peterson et al. | 427/388.1 |
| 4,501,834 | 2/1985 | Su | 424/73 |
| 4,624,051 | 11/1986 | Apprille, Jr. et al. | 30/50 |
| 4,639,480 | 1/1987 | Birum et al. | 524/104 |

FOREIGN PATENT DOCUMENTS

| | | | |
|---|---|---|---|
| 184440 | 6/1986 | European Pat. Off. . | |
| 2340805 | 2/1974 | Fed. Rep. of Germany | 30/41 |
| 2009017A | 6/1979 | United Kingdom . | |
| 2024082A | 1/1980 | United Kingdom . | |
| 2024082 | 1/1980 | United Kingdom | 30/41 |

*Primary Examiner*—Douglas D. Watts
*Assistant Examiner*—Paul M. Heyrana, Sr.
*Attorney, Agent, or Firm*—Finnegan, Henderson, Farabow, Garrett & Dunner

[57] ABSTRACT

A razor blade unit comprising a support for at least one razor blade and a surface for slidably engaging the skin of a user, and a xerogel on the surface. A process for making a sliding surface on a razor blade unit comprising applying a solution of polyurethane, a water-soluble plastic and a solvent to a surface of the razor blade unit which engages the skin of a user during shaving, and evaporating the solvent to form the sliding surface.

44 Claims, 2 Drawing Sheets

RAZOR AND PROCESS FOR MANUFACTURING A SURFACE OF LOW FRICTIONAL RESISTANCE ON A RAZOR

This application is a continuation of application Ser. No. 07/285,175, filed 12/16/88 abandoned 1/30/91.

The invention concerns a razor with a platform for at least one razor blade, where a surface in contact with the skin of the user during the shaving process is provided with a lubricant and a process for manufacturing such a surface with low frictional resistance on a safety razor.

Various aids are known for wet shaving which should perform the task of reducing the frictional resistance between skin and a razor during the shaving process, namely shaving foam, shaving soap, stubble softening agents as well as medical or cosmetic substances or combinations of all these. Such shaving aids reduce either the cutting work which has to be done to separate the stubble by softening the stubble or act as a lubricant which reduces the frictional force between the plastic parts of the safety razor in contact with the skin of the user.

It was proposed to use polyethylene oxide as an intergal, water-soluble shaving aid on a razor or to fit an injection molded strip of a hydrophobic polymer, such as polystyrene, and a hydrophilic polymer, such as polyethylene oxide, in a recess on the cap of the razor. In both cases the endeavor is to continuously dissolve out the water-soluble polymer components during the course of the wet shave, and to produce a sliding film on the skin. This reduces the frictional forces occurring during shaving and makes the shaving process softer and more comfortable.

However, there are disadvantages in using such shaving aids. The water-soluble, polymeric material that dissolves out during the shaving process forms a film on the skin of the user which dries on the already shaved skin surfaces. It is thus necessary to wash off the dried-on lubricant from the skin after shaving, which may be difficult depending on the degree of hardness of the water available and can possibly leave a sticky feeling with the user. Some of the residues of the dissolved out lubricant inevitably remain on the skin and with repeated use, the risk of dangerous skin irrations become a serious problem.

In addition, the dissolving or leaching out of the lubricant during the shaving process is uncontrollable. The rate at which the lubricant leaches out is dependent on many factors such as the temperature of the water used, the time the razor remains immersed in the water, the shaving time and the number of shaving strokes. Typically, when the shaving aid is at the end of its useful life, only slight amount of lubricant is given off. It is at this point, when the cutting action and shaving comfort of the razor blade have deteriorated through wear, that the additional lubricant effect is needed. However, an adequate quantity of lubricant is no longer adequately available.

Finally, the method of making razor blade units and/or razors with such sliding strips is very costly. They can be produced by either injection molding of the cap and sliding strip separately (which can subsequently be joined together by bonding), or by an expensive 2-component injection molding process. Also, the high costs of the water-soluble polymers used as lubricants add to production costs.

It has therefore been proven in practice that even with the use of sliding strips on razors which contain a water-soluble polymer as a lubricant, shaving aids such as shaving foam or shaving cream cannot be dispensed with, as was originally intended with these sliding strips.

It is therefore an object of the present invention to provide a method of making razor which overcomes the disadvantages associated with razors that contain water-soluble shaving aids.

Another object of the present invention is to provide a razor having a highly slidable surface when wet. This is particularly suprising given the fact that the coefficient of friction between skin and polystyrene (the usual material of razors) is considerably greater when the skin is wet then when it is dry.

Additional objects and disadvantages of the invention will be set forth in the description which follows and in part will be apparent from the description, or may be learned by practice of the invention. The objects and advantages of the invention may be realized and obtained by means of the instrumentabilities and combinations particularly pointed out in the appended claims.

To achieve the foregoing objects and in accordance with the purposes of the invention as embodied and broadly described herein there is provided a razor blade unit comprising a support for at least one razor blade, a surface for slideably engaging the skin of a user and a xerogel on the surface. The support is preferably a platform. The xerogel becomes a lyogel with a coefficient of friction less than 0.25 upon absorption of a dispersion medium and is highly slidable on the user's skin. The dispersion medium is preferably hydrous, e.g. water. Advantageously, the razor of the present invention reduces the frictional forces occuring between the razor's surface and a user's skin without the use of a water-soluble, polymeric film forming agent.

The surface of the razor is highly slidable on the skin of a user because of the properties of the wetted xerogel. Xerogels are gels which have lost their fluidity in some way, e.g. by evaporation. The basic gel structure is, however, retained and comprises one or more colloidally distributed substance with long or heavily branched particles and a liquid (usually water) as the dispersion medium. The colloidally distributed substance forms a spatial network in the dispersion medium when the particles adhere to each other at various points (adhesion points) due to secondary or primary valences. If the spaces between the particles are filled with liquid, it is called a lyogel. The xerogels produced by evaporation represent a boundary state with the solid. By adding the dispersion medium, e.g. water, xerogels swell again into lyogels. The surface becomes slippery and has a low coeficient of friction. Accordingly, the collodial substance forming the network does not pass into solution, and consequently, an irritating film of a dissolved out lubricant is not formed on the skin of the user during shaving.

Preferably the xerogel are comprised of a natural unary system, such as polysaccharides of high molecular weight, or a homogeneous mixture of homopolymers and copolymers of vinyl pyrrolidone, preferably polyvinyl pyrrolidone, as well as an aromatic polyurethane. Absorption of water during the shaving process produces the high slidability but does not induce the leaching out of substances because of the intermolecular forces typical in such gels.

In a xerogel comprising polyvinyl pyrrolidone (PVP) and polyurethane (PUR) it is preferable to have a ratio PVP:PUR of (3-5):1, (i.e., there is a 3-5 fold surplus of PVP), and more preferably between (3.6-4):1. This ratio is preferred to achieve a low coefficient of friction, the value of which is retained over the life of the razor (normally seven days). This ratio is also preferred to obtain optimal resistance to wear as well as a reduction in drying time during the manufacture of the razor.

With respect to the manufacture of the razor, the following dependences are noted:

1. The more polyvinyl pyrrolidone there is in the xerogel, the lower the coefficient of friction.

2. The greater the relative amount of polyvinyl pyrrolidone in the xerogel, the greater the risk that the intermolecular linkage forces thereof are not sufficient to hold the polyvinyl pyrrolidone in the gel structure, thereby increasing the risk of polyvinyl pyrrolidone dissolving out.

3. Abrasion resistance increases with the proportion of polyurethane.

A particularly preferred embodiment is a dispersion of polyurethane with water and N-methyl pyrrolidone (NMP) as a solvent. It is preferred that the polyurethane dispersion have a solids content between 30 and 33% by weight, more preferably 31% by weight. The preferred content of the (NMP) is from about 10 to 12% by weight, more preferably 11% by weight. The balance is water. NMP is a high boiling solvent with a boiling point of about 204° C. This results in a lengthening of the evaporation time, which is acceptable since NMP is highly environmentally compatibile. The usual organic solvents can therefore be avoided.

According to another preferred embodiment, the xerogel is applied to the surface of the razor in a thickness from about 5 to and 150 $\mu$m. The surface that engages the skin may include a cap or guardbar. Preferably the coating thickness is less than 30 $\mu$m, which is sufficiently stable even in the swollen state of the lyogel. Although a thickness of about 160 $\mu$m is acceptable, if the coating thicknesses is greater than 150 $\mu$m, losses of material can occur due to abrasive forces. A correspondingly high absorption of water (swelling capacity) reduces the resistance to abrasive forces.

The coating can be formed either directly or indirectly on a surface of the razor which contacts the skin of the user during shaving. For indirect formation, it is proposed in another embodiment of the invention to apply the xerogel to a self-adhesive carrier film which is arranged on the surface of the razor that engages the skin of a user during shaving. The carrier film is selected from a material consisting of polyvinyl chloride and polyester. To improve adhesion, it is preferred to affix the coated carrier film either on a flat part of the razor or on a curved part having a radius (R) greater than 20 $\mu$m. This ensures adequate adhesion on the razor and evenly distributes frictional forces over the whole sliding surface. When using a carrier film it is preferred to arrange it in a recess of the razor surface, such as in the cap, to achieve an even contact surface.

A razor according to the present invention has a short activation time. This is because the structure of the xerogel is such that small molecules, like that of water, can penetrate into the gel network and bring about swelling of the xerogel within a short time. The activation time can be controlled by the choice of matrix material and the width of the gel network.

Unlike the deterioration of the sliding properties experienced over the useful life of the prior art razors, the razors of the present invention continue to exhibit excellent sliding properties with increased use due to the orientation of the molecular chains of the xerogel at the surface.

Resistance to leaching out of vinyl pyrrolidone is considerably improved with the razor of the present invention. Even 24 hours of immersion in water does not change the sliding properties of the xerogel coating. Furthermore, storage at high humidity (>90%), which causes prior art lubricants to become unusable, has no effect on the quality of the razor of the present invention. Finally, the temperature stability of the xerogel is very high, as it is basically determined by the temperature stability of the carrier material. This results in problem-free handling for the user and assured sliding characteristics over the useful life of the razor or the razor blade unit.

The present invention is also directed to a method for making a sliding surface or razor comprising applying a solution of a polyurethane, a water-soluble polymer, in particular polyvinyl pyrrolidone, and a solvent to the surface and evaporating the solvent to form the sliding surface on the razor. The polyurethane is preferably a linear unlinked polyurethane. The solution can be applied directly or indirectly in one operation as a coating to the surface, and preferably to the cap of the razor. The solvent is evaporated to form a xerogel by heating the solution. By this method, a xerogel is obtained in one step immediately after evaporation of the solvent without additional curing, so that the cost in time and technique for making the sliding coating is reduced to a minimum, which enables massproduction of the razors of the instant invention.

For indirect application, a self-adhesive carrier film of polyvinyl chloride or polyester, preferably polyethylene phthalate, is treated with a caustic or polymer bonding aid. The treated carrier film is coated with the above solution and the solvent is evaporated. The coated carrier film is joined to the surface of the razor, preferably the cap, by bonding.

It may also be appropriate with the direct application method to carry out pretreatment of the surface with a primer or to pretreat the surface to improve adhesion with a solution of chromatisulphuric acid for 15 minutes at a temperature of preferably 40° C. The treated surface then used is an ABS suitable for electroplating.

It is preferred in the present method of making the sliding surface on the razor to use a homogeneous mixture of polyurethane and polyvinyl pyrrolidone, wherein the ratio by weight of polyvinyl pyrrolidone to polyurethane is from about 3:1 to 5:1. The homogeneity of the mixture is ensured by continuously stirring the solution until it is applied to the surface to be coated. The evaporation step is conducted after application and preferably done at a temperature of about 70° C. over a period of less than 15 min.

The method of the present invention can advantageously be adapted to a mass production arrangement and still produce sliding surfaces on the razors in which the xerogel on the carrier material is firmly secured.

The following examples are presented to provide a more complete understanding of the invention. They are merely exemplary and should not be construed as limiting the scope of the invention.

EXAMPLE 1

A polyvinyl pyrrolidone/polyurethane blend was made to the following formulation:

| | |
|---|---|
| Polyurethane dispersion | 81 g |
| Water | 250 g |
| Diacetone alcohol | 50 g |
| Polyvinyl pyrrolidone K90 | 100 g |
| Isopropanol | 519 g |
| Fluorad FC430 | 1 g |

The cap of a safety razor was immersed in the above solution and then subjected to drying for 10 min. at 70° C. It may be advantageous to further dilute the dip solution. A xerogel was formed which during shaving absorbed water as a dispersion medium and obtained highly slidable surface characteristics.

EXAMPLE 2

The following mixture of polyvinyl pyrrolidone and polyurethane was used:

| | |
|---|---|
| Polyurethane dispersion | 81 g |
| Water | 300 g |
| Diacetone alcohol | 60 g |
| Polyvinyl pyrrolidone K90 | 90 g |
| Isopropanol | 469 g |
| Fluorad FC430 | 1 g |

The solution of these substances was applied to a polyvinyl chloride film 150 μm thick and the solvent evaporated within 10 minutes at 75° C. The PVC film thus coated was cut into strips. A strip was joined with the cap of a safety razor by bonding. A waterproof polyacrylate from 10 to 15 μm thick was used as the adhesive for bonding.

Further details, features and advantages of the subject matter of the patented invention can be seen from the following description of the accompanying drawings.

Figure 1:
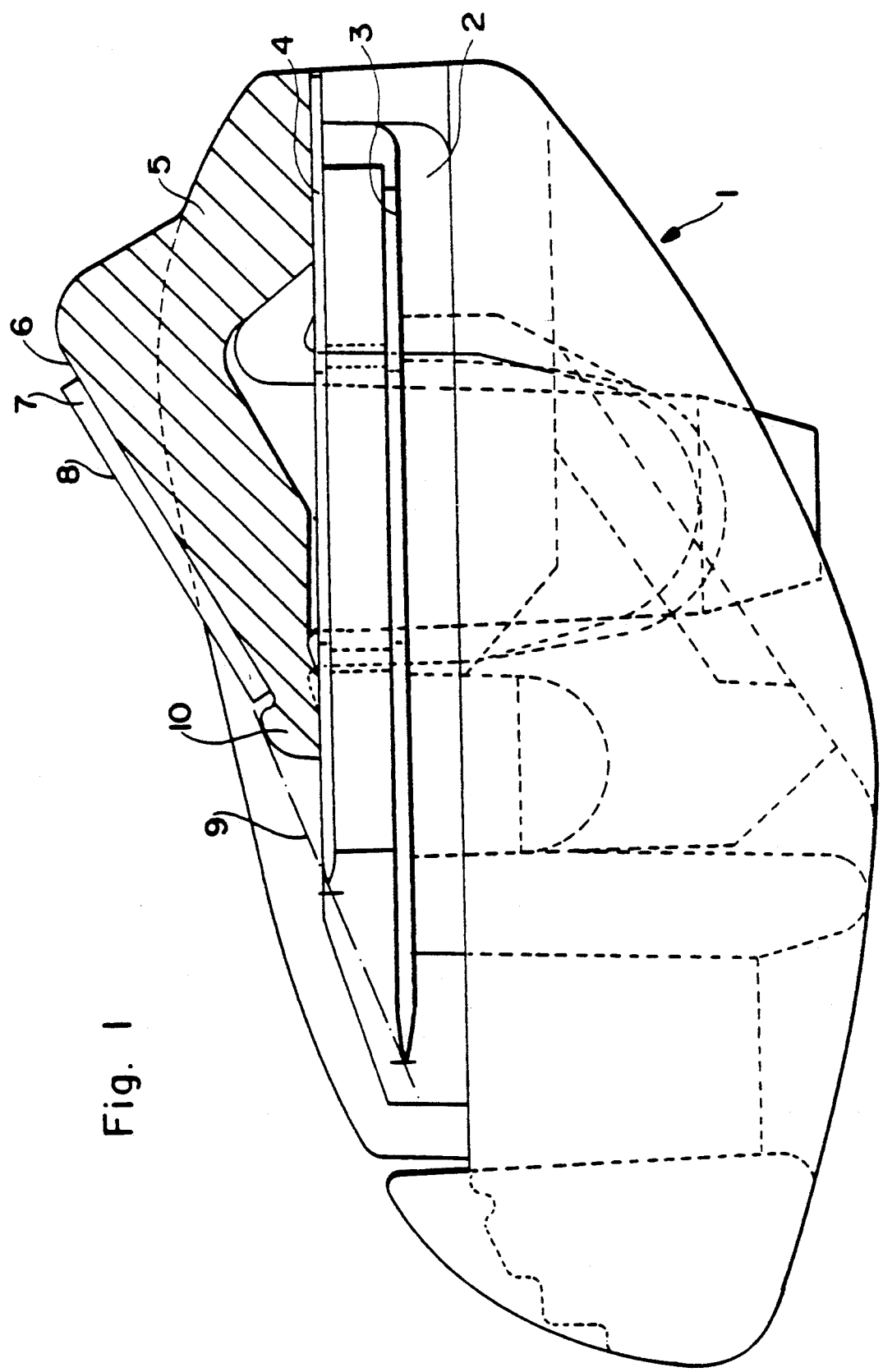
FIG. 1 is a razor blade unit, partially in section.

The razor blade unit 1 in FIG. 1 is joined in a known manner to a razor handle fitted with suitable fastenings and forms the razor to be used during shaving. It has a platform 2 for two razor blades 3, 4 and a cap 5. A flat surface 6 is shaped on the front of cap 5 which is suitable for housing a coated carrier film or a sliding strip 7. The flat surface 6 ends in the front in a rounded protective lip or a guardbar 10, which is used firstly to facilitate positioning of the sliding strip 7 on assembly and secondly to protect the front edge during shaving. Its construction can be seen from FIGS. 2 and 3 of the drawing. The sliding strip 7 has on the front a sliding surface 8 made from xerogel, which is so arranged in relation to the front end of cap 5 that a smooth transition is created from an imaginary connecting line forming a tangent with the cutting edges of the two razor blades via the front end of cap 5 to the sliding surface 8 in the direction of the shaving movement to be made. The sliding surface 8 is angled slightly forward to the geometric imaginary line 9 connecting the cutting edges of the two razor blades to ensure increased skin contact when used.

Figure 2:
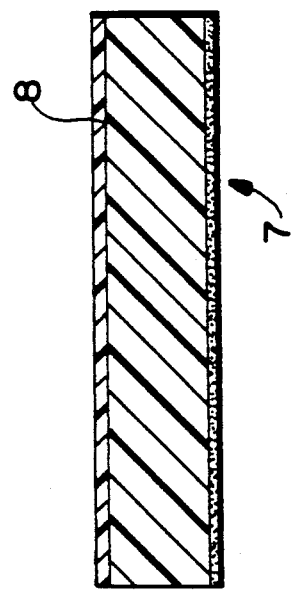
FIG. 2 is an individual sliding strip for use on a razor blade unit as in FIG. 1 in section.

According to FIG. 2 of the drawing the sliding strip 7 is comprised of several layers. The middle layer is a polyvinyl chloride carrier film 150 μm±10% thick, the bottom of which is coated with a polyacrylate adhesive. The top is applied with a coating of a polyvinyl pyrrolidone/ a thickness of 25 μm±5%.

Figure 3:
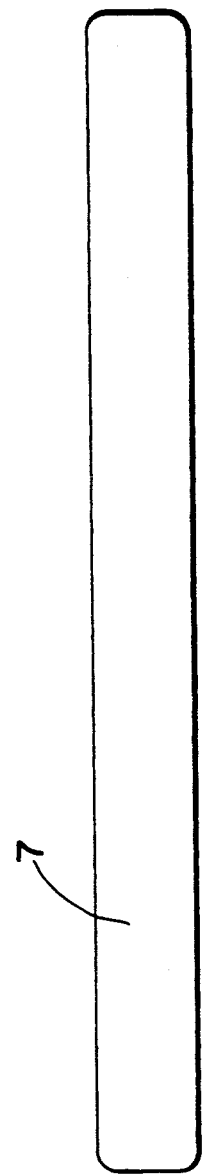
FIG. 3 is a top view of the sliding strip.

Such a sliding strip 7 with sliding surface 8 is bonded on a razor blade unit 1 with the waterproof polyacrylate adhesive layer, which is 10 to 15 μm thick. The rounded corners as seen in FIG. 3 are provided to improve this process. When the safety razor is used, a lyogel with excellent sliding properties forms almost spontaneously when the xerogel absorbs water. Accordingly the razor of the present invention reduces the coefficient of friction between the razor surface and the user's skin which significantly reduces the surface work to be done when shaving so that a comfortable and efficient shave is achieved. Furthermore, no appreciable wear of the sliding surface 8 due to abrasion can be found over the usual life of the razor blades 3, 4.

What is claimed is:

1. A razor blade unit comprising a support for at least one razor blade, a surface for slidably engaging the skin of a user, and a xerogel on the surface, wherein the xerogel comprises a homogeneous mixture of homopolymers and copolymers of polyvinyl pyrrolidone with polyurethane in which the ratio of the amount of polyvinyl pyrrolidone to polyurethane is about (3-5):1.

2. The razor blade unit of claim 1, wherein the xerogel has a coefficient of friction less than 0.25 when contacted with a dispersion medium.

3. The razor blade unit of claim 1, wherein the xerogel has a coefficient of friction less than 0.25 when contacted with a hydrous dispersion medium.

4. The razor blade unit of claim 1, wherein the polyurethane is an aromatic polyurethane.

5. The razor blade unit of claim 1, wherein the ratio of polyvinyl pyrrolidone to polyurethane is about (3.6-4):1.

6. The razor blade unit of claim 1, wherein the polyurethane is a dispersion with water and N-methylpyrrolidone as a solvent, the polyurethane dispersion has a solids content between 30 and 33% by weight, the N-methyl pyrrolidone is from about 10 to 12% by weight and the balance is water.

7. The razor blade unit of claim 6, wherein the solids content of the polyurethane is 31% by weight and the N-methyl pyrrolidone is 11% by weight.

8. The razor blade unit of claim 1, including a cap and wherein the xerogel is disposed on the cap.

9. The razor blade unit of claim 8, wherein the xerogel is on a carrier film bonded to the cap.

10. The razor blade unit of claim 9, wherein the surface includes a recess where the carrier film is bonded.

11. The razor of claim 10, wherein the recess is a flat surface, and the front-end of the recess forms a rounded protective lip being about equivalent in height to the thickness of the carrier film and the xerogel.

12. The razor as in claim 10, wherein the xerogel and carrier film is angled forward from the plane of shaving to give increased skin contact.

13. The razor blade unit of claim 1, including a guardbar, and wherein the xerogel is disposed on the guardbar.

14. The razor blade unit of claim 1; including a cap and a guardbar, and wherein the xerogel is disposed on both the guardbar and cap.

15. The razor blade unit of claim 1, wherein the thickness of the xerogel is in the range of about 5 to 160 μm.

16. The razor blade unit of claim 1, wherein the thickness of the xerogel is less than 30 μm.

17. The razor blade unit of claim 1, wherein the xerogel is on a carrier film bonded to the surface.

18. The razor blade unit of claim 17, wherein the surface includes a recess where the carrier film is bonded.

19. The razor blade unit of claim 17, wherein the carrier film is polyvinyl chloride.

20. The razor blade unit of claim 17, wherein the carrier film is polyester.

21. The razor blade unit of claim 17, wherein the carrier film is polyethylene phthalate.

22. The razor blade unit of claim 17, wherein the carrier film is arranged on a flat portion of the cap.

23. The razor blade unit of claim 17, wherein the carrier film is arranged on a curved portion of the cap having a radius greater than 20 μm.

24. A process for making a sliding surface on a razor blade unit comprising forming a solution of polyurethane, polyvinyl pyrrolidone and a solvent, wherein the weight of polyvinyl pyrrolidone to polyurethane is in the range of about 3:1 to 5:1, evaporating the solvent to form a xerogel, and bonding the xerogel to a surface of the razor blade unit which engages the skin of a user during shaving.

25. The process of claim 24, wherein the polyurethane is linear unlinked polyurethane.

26. The process of claim 24, wherein the forming step includes applying the solution to a carrier film.

27. The process of claim 26, wherein the carrier film is polyvinyl chloride.

28. The process of claim 26, wherein the carrier film is polyester.

29. The process of claim 26, wherein the carrier film is polyethylene phthalate.

30. The process of claim 26, including pretreating the carrier film with a bonding aid prior to the bonding step.

31. The process of claim 30, wherein the bonding aid is caustic.

32. The process of claim 31, wherein the bonding aid is a polymer.

33. The process of claim 24, including pretreating the surface of the razor blade unit in a solution of chromati-sulphuric acid.

34. The process of claim 33, wherein the pretreating occurs for about 15 minutes at a raised temperature.

35. The process of claim 34, wherein the raised temperature is about 40° C.

36. The process of claim 24, wherein the solution is a homogeneous mixture of polyurethane and polyvinyl pyrrolidone.

37. The process of claim 36, including the step of constantly stirring the solution to ensure homogeneity.

38. The process of claim 24, wherein the evaporating step is carried out at a temperature of greater than 70° C. for a time of less than 15 minutes.

39. A process for making a sliding surface on a razor blade unit comprising applying a solution of polyurethane and polyvinyl pyrrolidone and a solvent to a surface of the razor blade unit which engages the skin of a user during shaving, wherein the weight of a polyvinyl pyrrolidone to polyurethane is in the range of about 3:1 to 5:1, and evaporating the solvent to form a xerogel.

40. The process of claim 39, wherein the polyurethane is linear unlinked polyurethane.

41. The process of claim 39, including pretreating the surface of the razor blade unit with a primer prior to the applying step.

42. The process of claim 39, wherein the solution is a homogeneous mixture of polyurethane and polyvinyl pyrrolidone.

43. The process of claim 42, including the step of constantly stirring the solution to ensure homogeneity.

44. The process of claim 39, wherein the evaporating step is carried out at a temperature of greater than 70° C. for a time of less than 15 minutes.

* * * * *